(12) United States Patent
Joo et al.

(10) Patent No.: US 8,216,686 B2
(45) Date of Patent: Jul. 10, 2012

(54) DENDRIMER WITH TRIPHENYLAMINE CORE, ORGANIC MEMORY DEVICE HAVING THE SAME, AND MANUFACTURING METHOD THEREOF

(75) Inventors: Won Jae Joo, Seongnam-si (KR); Tae Lim Choi, Suwon-si (KR); Chulhee Kim, Seongnam-si (KR); Kwang Hee Lee, Suwon-si (KR)

(73) Assignee: Samsung Electronics Co., Ltd., Gyeonggi-do (KR)

(*) Notice: Subject to any disclaimer, the term of this patent is extended or adjusted under 35 U.S.C. 154(b) by 1030 days.

(21) Appl. No.: 12/007,308

(22) Filed: Jan. 9, 2008

(65) Prior Publication Data

US 2008/0248330 A1    Oct. 9, 2008

(30) Foreign Application Priority Data

Apr. 3, 2007   (KR) .................. 10-2007-0032774

(51) Int. Cl.
*B32B 15/04* (2006.01)
*B32B 9/04* (2006.01)
*H01L 51/00* (2006.01)

(52) U.S. Cl. ........ 428/469; 428/457; 428/688; 428/689; 428/702; 428/704; 257/40; 427/58

(58) Field of Classification Search .................. None
See application file for complete search history.

(56) References Cited

U.S. PATENT DOCUMENTS

| | | | |
|---|---|---|---|
| 6,055,180 A | 4/2000 | Gudesen et al. | |
| 6,558,818 B1 * | 5/2003 | Samuel et al. | 428/690 |
| 6,699,597 B2 * | 3/2004 | Bellmann et al. | 428/690 |
| 2002/0163057 A1 | 11/2002 | Bulovic et al. | |

FOREIGN PATENT DOCUMENTS

JP    62-095882    5/1987

OTHER PUBLICATIONS

R. S. Potember et al., "Electrical Switching and Memory Phenomena in Cu-TCNQ Thin, Films", Applied Physics Laboratory, 34, Jan. 10, 1979, pp. 405-407.
Anirban Bandyopadhyay et al., "Large Conductance Switching and Memory Effects in Organic Molecules for Data-Storage Applications", Applied Physics Laboratory, 82 (2003), pp. 1215-1217.
Himadri Majumdar et al., "Data-Storage Devices Based on Layer-By-Layer Self-Assembled Films of a Phthalocyanine Derivative" Organic Electronics 4 (2003), pp. 39-44.
Himadri Majumdar et al., "Conductance Switching and Data-Storage in Oriented Polymer-Based Devices: Impedance Characteristics", Thin Solid Film 446 (2004), pp. 296-300.

* cited by examiner

*Primary Examiner* — Monique Jackson
(74) *Attorney, Agent, or Firm* — Harness, Dickey & Pierce, P.L.C.

(57) ABSTRACT

A dendrimer according to example embodiments may include a triphenylamine core, wherein a conjugated dendron having no heteroatoms is coupled to the triphenylamine core. An organic memory device according to example embodiments may include an organic active layer between a first electrode and a second electrode, wherein the organic active layer includes the dendrimer according to example embodiments. A barrier layer may be provided between the first and second electrodes. A method of manufacturing the organic memory device according to example embodiments may include forming an organic active layer between a first electrode and a second electrode, the organic active layer including the dendrimer according to example embodiments.

10 Claims, 6 Drawing Sheets

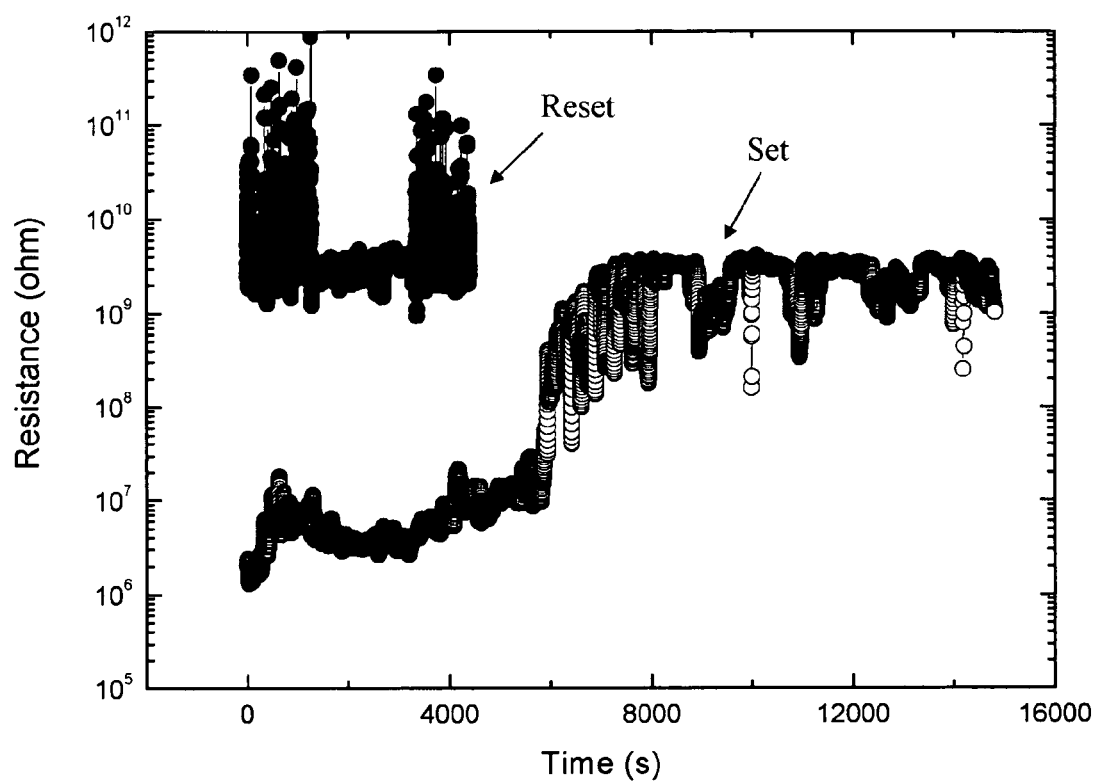

DENDRIMER WITH TRIPHENYLAMINE CORE, ORGANIC MEMORY DEVICE HAVING THE SAME, AND MANUFACTURING METHOD THEREOF

PRIORITY STATEMENT

This non-provisional application claims priority under 35 U.S.C. §119 to Korean Patent Application No. 10-2007-0032774, filed on Apr. 3, 2007 in the Korean Intellectual Property Office (KIPO), the entire contents of which are incorporated herein by reference.

BACKGROUND

1. Field

Example embodiments relate to a dendrimer, an organic memory device having the dendrimer, and a method of manufacturing the organic memory device.

2. Description of the Related Art

The demand for memory devices has increased with the growth of information and communication industries. For example, the use of portable computers or electronic apparatuses (e.g., portable terminals, smart cards, electronic cash, personal digital assistants, digital audio players, and multimedia players) has increased. The memory devices for these apparatuses may be nonvolatile memory devices, wherein recorded information is not erased when power sources are turned off.

As LSI (Large Scale Integration) technologies advance, the number of bits of memory integrated in an IC chip may attain megabit levels. Thus, submicron circuit line width may be required. Conventional nonvolatile memory devices may be memory devices based on a standard silicon process. However, these conventional memory devices may have a more complex structure and larger-sized memory cells. Consequently, realizing higher capacity memory devices may be more difficult. Furthermore, a fining process, wherein line width per unit area is decreased, may be required to obtain higher integrated memory capacities for memories based on silicon. As a result, the manufacturing cost of memory chips may increase, and further miniaturization of the memory chips may be restricted by technical limitations, thus decreasing profitability.

Accordingly, next-generation memories having higher speeds, higher capacities, and lower power consumption are being developed as suitable alternatives to conventional memories for developing wireless portable information and communication systems and apparatuses for processing relatively large amounts of information. Types of next-generation memories may include ferroelectric RAM, ferromagnetic RAM, phase change RAM, nanotube RAM, holographic memory, and organic memory, depending on the material constituting a cell, which is a basic unit in a semiconductor. Among the next-generation memories, organic memories may realize memory properties by using the bistability of voltage values obtained by introducing an organic material between the upper and lower electrodes and applying a voltage thereto. Thus, organic memories may overcome limits of processibility, manufacturing costs, and degrees of integration (disadvantages of conventional flash memory) while realizing nonvolatility (advantage of conventional flash memory).

A conventional semiconductor device may include an intermediate layer provided between the upper and lower electrodes, wherein the intermediate layer may be formed by mixing an ionic salt (e.g., NaCl or CsCl) with a conductive polymer. The semiconductor device may realize switching and memory characteristics by exploiting a charge separation phenomenon caused by an electric field. However, when the semiconductor device is manufactured using the conductive polymer, realizing accurate molecular weight and distribution may be more difficult even if spin coating may be performed. Thus, reproduction of the intermediate layer may not be easy, thereby resulting in less uniform device characteristics.

A conventional memory device may use ferroelectricity based on the crystalline state of fluorine polymers (e.g., poly(vinyldifluoroethylene)). However, when a memory device is manufactured using fluorine polymer, a coating process may be more difficult to perform because of the hydrophobicity of fluorine, thereby decreasing processibility. Furthermore, information may be recorded only once and must be read optically, thereby increasing the size and complexity of the device.

SUMMARY

A dendrimer according to example embodiments may include a triphenylamine core, wherein a conjugated dendron having no heteroatoms is coupled to the triphenylamine core. The dendrimer may be represented by Formula 1,

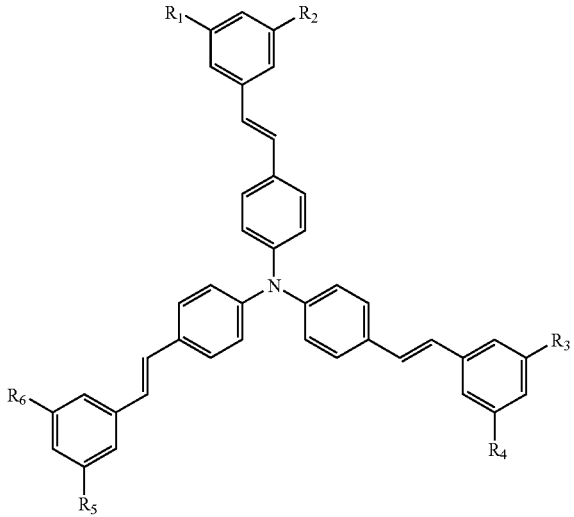

Formula 1 wherein $R_1$, $R_2$, $R_3$, $R_4$, $R_5$, and $R_6$ may be selected from the group consisting of acetylene, vinylene phenylene, fluorene, phenylene ethynylene, naphthalene, anthracene, tetracene, perylene, and pyrene; and substituents of $R_1$, $R_2$, $R_3$, $R_4$, $R_5$, and $R_6$ may be selected from the group consisting of $C_1$-$C_{20}$ alkyl, $C_3$-$C_{20}$ cycloalkyl, $C_5$-$C_{30}$ heterocycloalkyl, $C_2$-$C_{20}$ alkenyl, $C_6$-$C_{20}$ aryl, $C_5$-$C_{30}$ heteroaryl, $C_7$-$C_{20}$ arylalkyl, and $C_7$-$C_{30}$ heteroarylalkyl.

The dendrimer represented by Formula 1 may be further represented by Formulas 2 to 4.
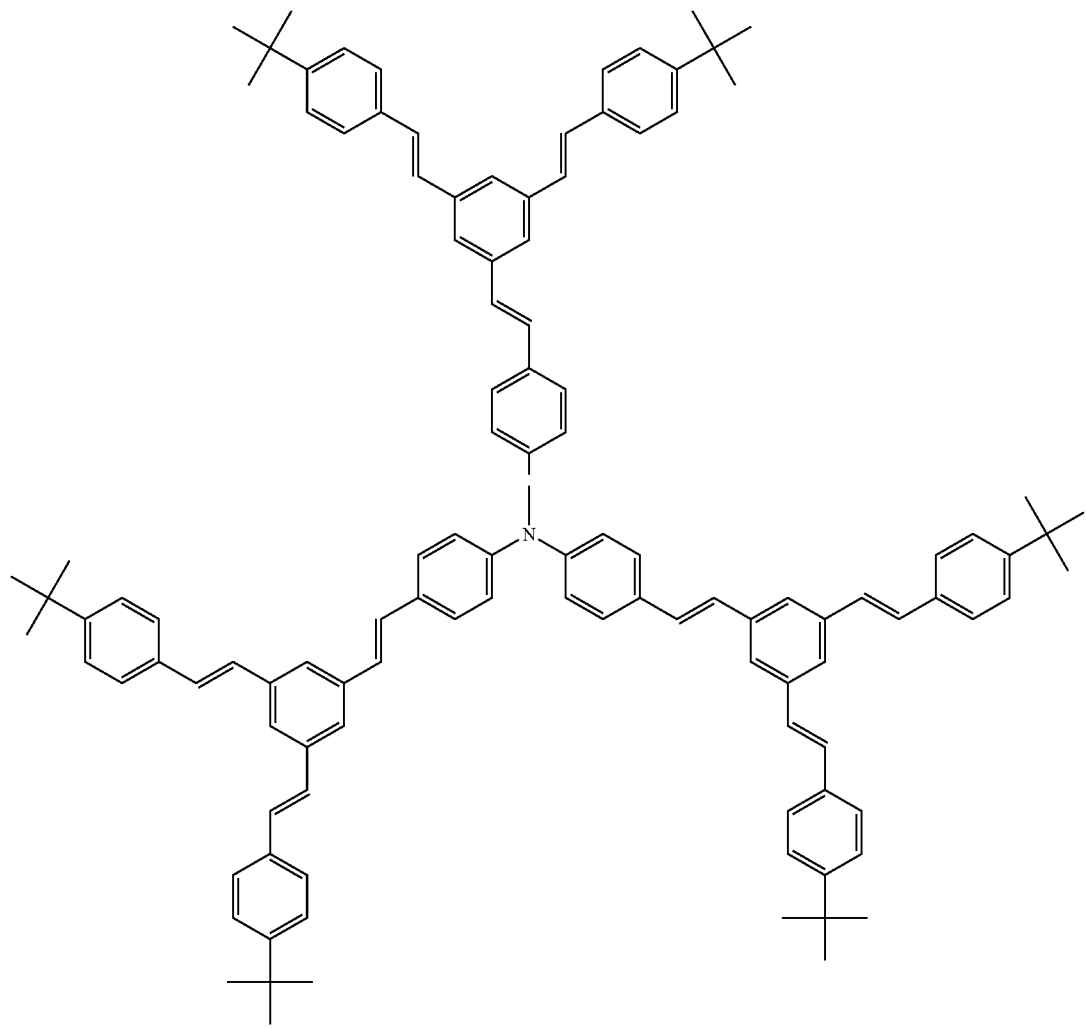
Formula 2
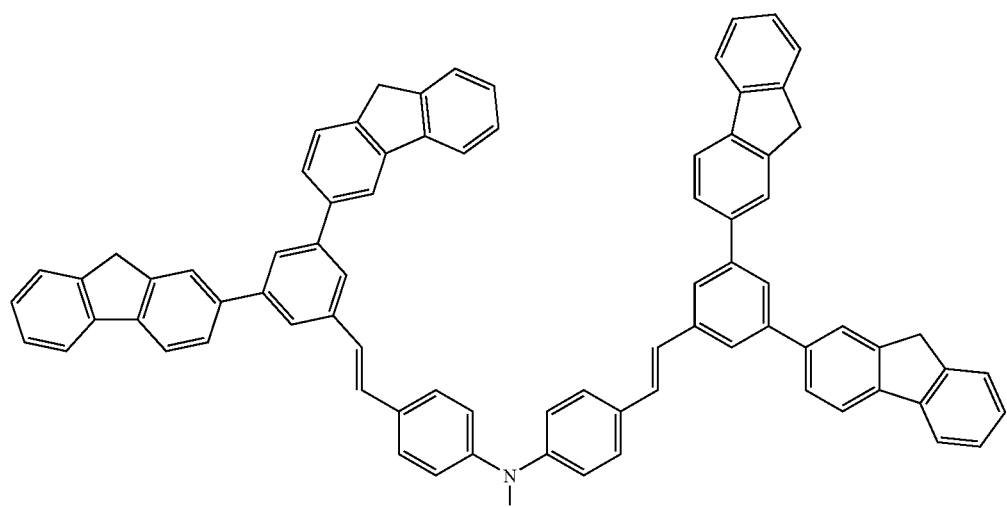
Formula 3

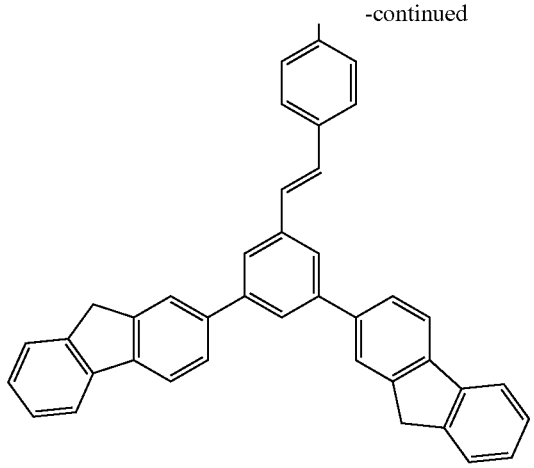

-continued

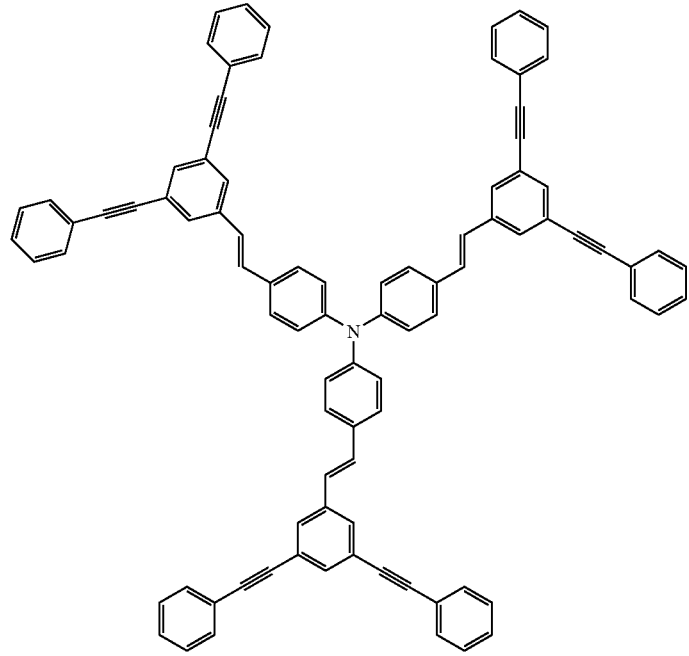

Formula 4

An organic memory device according to example embodiments may include an organic active layer between a first electrode and a second electrode, the organic active layer including a dendrimer having a triphenylamine core, wherein a conjugated dendron having no heteroatoms is coupled to the triphenylamine core. The organic memory device according to example embodiments may be manufactured with a simpler process at a lower cost and may exhibit nonvolatility. The organic memory device may also have higher integration, lower power consumption, and higher-speed switching characteristics.

A method of manufacturing an organic memory device according to example embodiments may include forming an organic active layer between a first electrode and a second electrode, the organic active layer including a dendrimer having a triphenylamine core, wherein a conjugated dendron having no heteroatoms is coupled to the triphenylamine core. The method according to example embodiments may include a simpler manufacturing process with lower temperature processing, thereby reducing manufacturing costs and applicable to the manufacture of a flexible memory device.

BRIEF DESCRIPTION OF THE DRAWINGS

Example embodiments may be more clearly understood from the following detailed description in conjunction with the accompanying drawings, in which:

FIG. 9 is a graph showing the variation of resistance based on time in the organic memory device manufactured in Example 1 according to example embodiments.

DETAILED DESCRIPTION OF EXAMPLE EMBODIMENTS

Figure 1:
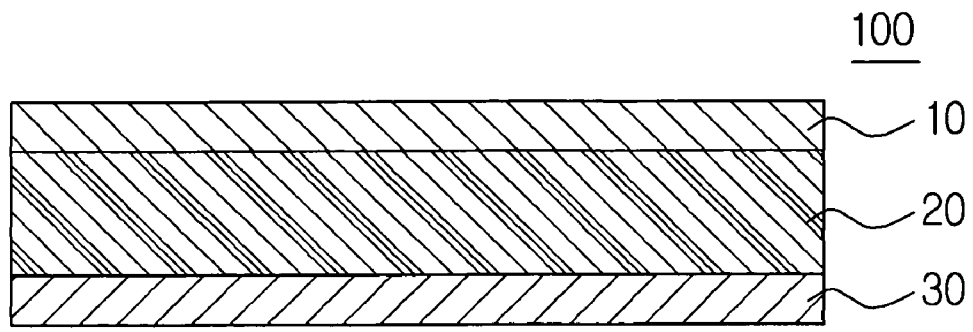
FIG. 1 is a schematic sectional view showing an organic memory device according to example embodiments.

Hereinafter, example embodiments will be described in detail with reference to the accompanying drawings. The same reference numerals are used throughout the different drawings to designate the same or similar components.

It will be understood that when an element or layer is referred to as being "on", "connected to", "coupled to", or "covering" another element or layer, it may be directly on, connected to, coupled to, or covering the other element or layer or intervening elements or layers may be present. In contrast, when an element is referred to as being "directly on," "directly connected to" or "directly coupled to" another element or layer, there are no intervening elements or layers present. Like numbers refer to like elements throughout the specification. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of example embodiments.

spatially relative terms, e.g., "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

The term "dendrimer" may refer to a material having a regularly repeating dendritic or radially-branched structure. A dendrimer may be formed into a spherical molecule by forming radial chains around a central core molecule. The branches of dendrimers may grow by steps while forming a layer, with each step referred to as a "generation."

Example embodiments provide a dendrimer having a triphenylamine core, in which a conjugated dendron having no heteroatoms is coupled to the triphenylamine core. The dendrimer according to example embodiments may be a lower molecular material in which triphenylamine, which may be an electron donor, may be used as a core, and a conjugated dendron having no heteroatoms is coupled to the triphenylamine core. Consequently, bistable memory characteristics may be realized because of the charge transfer between the triphenylamine core and the conjugated dendron in the dendrimer. Because the dendrimer having a triphenylamine core may be a lower-molecular and soluble material, an organic active layer of an organic memory device may be formed using the dendrimer in a solution process, e.g., a spin coating process. The molecular weight of the dendrimer having a triphenylamine core may be in the range of about 1000 to about 10,000.

The conjugated dendrons of the dendrimer may be identical to or different from each other and one or more may be independently selected from the group consisting of substituted or unsubstituted acetylene, vinylene phenylene, fluorene, phenylene ethynylene, naphthalene, anthracene, tetracene, perylene, and pyrene.

The conjugated dendrons of the dendrimer may have one or more substituted groups or substituents. The substituted groups may be identical to or different from each other and may include, but are not limited to, an alkyl group of $C_1$-$C_{20}$, a cycloalkyl group of $C_3$-$C_{20}$, a heterocycloalkyl group of $C_5$-$C_{30}$, an alkenyl group of $C_2$-$C_{20}$, an aryl group of $C_6$-$C_{20}$, a heteroaryl group of $C_5$-$C_{30}$, an arylalkyl group of $C_7$-$C_{20}$, and a heteroarylalkyl group of $C_7$-$C_{30}$.

The alkyl group may include a methyl group, an ethyl group, a propyl group, an isobutyl group, a sec-butyl group, a tert-butyl group, a pentyl group, an iso-amyl group, and a hexyl group, wherein the groups may be straight-chained or branched.

The cycloalkyl group may refer to a monovalent monocyclic system of about 3 to about 20 carbon atoms. One or more hydrogen atoms of the cycloalkyl group may be substituted. The heterocycloalkyl group may refer to a monovalent monocyclic system of about 5 to about 30 ring atoms, which may include about one to three ring heteroatoms selected from among N, O, P, and S. The residual ring atoms may be Cs, and one or more hydrogen atoms of the heterocycloalkyl group may be substituted.

The alkenyl group may include a vinyl group, an allyl group, a propenyl group, a butenyl group, a hexenyl group, and a cyclohexenyl group. The aryl group may refer to a carbocyclic aromatic system having one or more aromatic rings, and the aromatic rings may be bonded and fused together through a pendent method. For example, the aryl group may include aromatic groups (e.g., a phenyl group, a naphthyl group, a tetrahydronaphthyl group). One or more hydrogen atoms of the aryl group may also be substituted.

The heteroaryl group may refer to a cyclic aromatic system of about 5 to about 30 ring atoms, which may include about one to three ring heteroatoms selected from among N, O, P, and S. The residual ring atoms may be Cs, and the rings may be bonded and fused together through a pendent method. One or more hydrogen atoms of the heteroaryl group may also be substituted.

The arylalkyl group may refer to a group in which some hydrogen atoms of the aryl group are substituted with lower alkyls. For example, the lower alkyls may be radicals (e.g., methyl, ethyl, propyl). The arylalkyl group may include a benzyl group and a phenylethyl group. One or more hydrogen atoms of the arylalkyl group may also be substituted.

The heteroarylalkyl group may refer to a group in which some hydrogen atoms of the heteroaryl group are substituted with lower alkyls. The heteroaryl group may be as described above. One or more hydrogen atoms of the heteroarylalkyl group may also be substituted with substitution groups, as in the alkyl group.

The dendrimer having a triphenylamine core according to example embodiments may be represented by Formula 1 below.

Formula 1

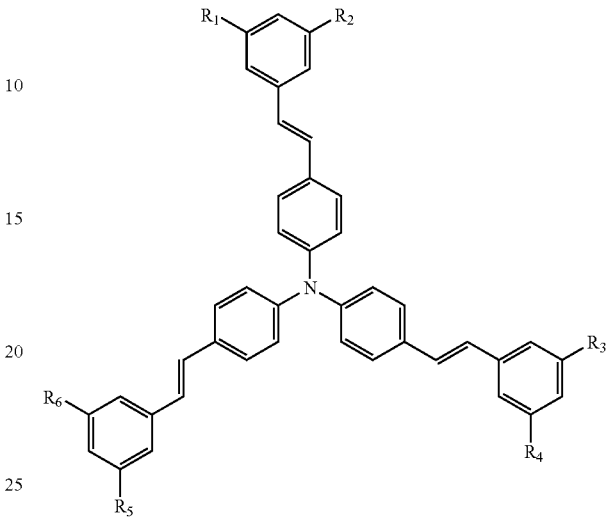

$R_1$, $R_2$, $R_3$, $R_4$, $R_5$, and $R_6$ may be identical to or different from each other, and one or more may be independently selected from the group consisting of substituted or unsubstituted acetylene, vinylene phenylene, fluorene, phenylene ethynylene, naphthalene, anthracene, tetracene, perylene, and pyrene.

Substituted groups of $R_1$, $R_2$, $R_3$, $R_4$, $R_5$, and $R_6$ may be identical to or different from each other and may be independently selected from the group consisting of an alkyl group of $C_1$-$C_{20}$, a cycloalkyl group of $C_3$-$C_{20}$, a heterocycloalkyl group of $C_5$-$C_{30}$, an alkenyl group of $C_2$-$C_{20}$, an aryl group of $C_6$-$C_{20}$, a heteroaryl group of $C_5$-$C_{30}$, an arylalkyl group of $C_7$-$C_{20}$, and a heteroarylalkyl group of $C_7$-$C_{30}$.

The dendrimer represented by Formula 1 above may be further represented by Formulas 2 to 4 below.

Formula 2

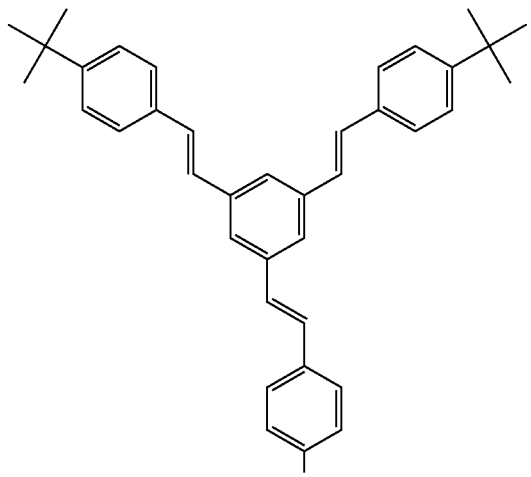

-continued
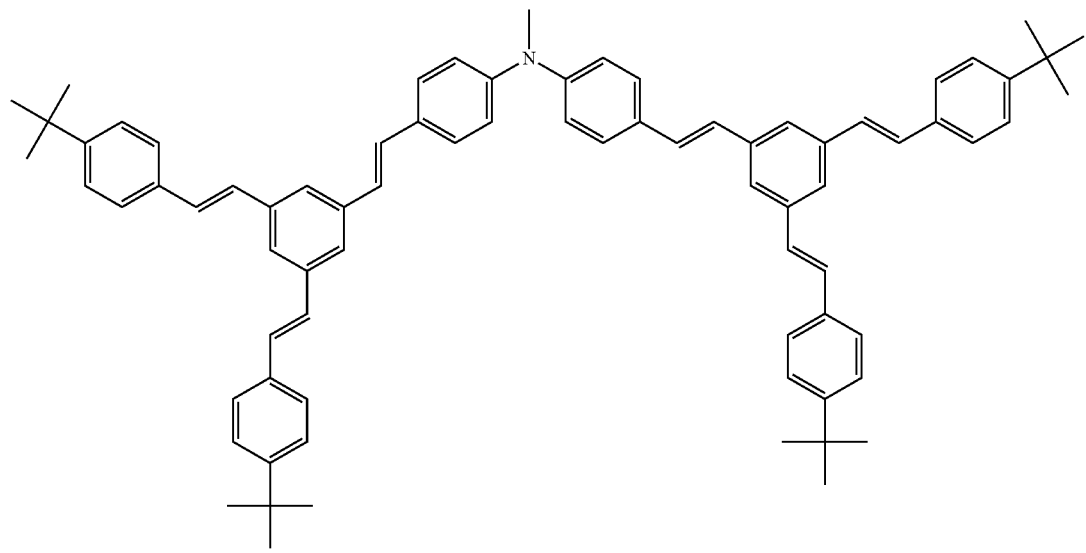
Formula 3
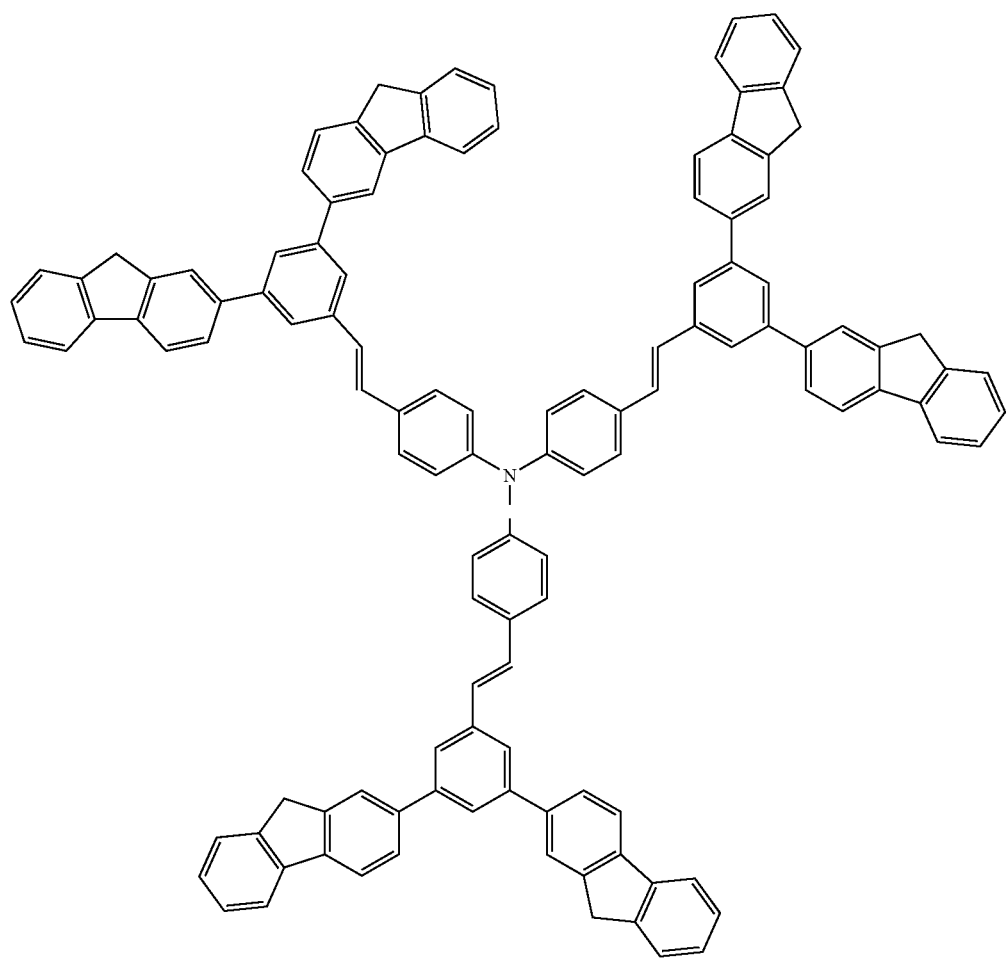

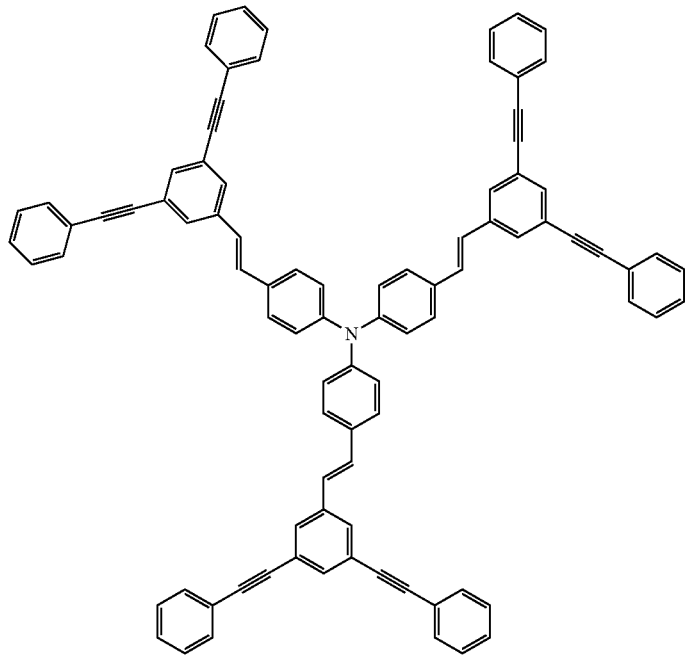

Formula 4

Dendrimers, unlike polymers, may have an advantage in that they may be synthesized to have a more accurate molecular weight and structure, and the material properties thereof after synthesis may be more predictable. In a polymer synthesizing process, a macromolecule may be formed through the partial decomposition and cross-linking of functional groups. In contrast, in a dendrimer synthesizing process, the dendrimer may be synthesized using a multi-step synthesis method, in which about two or three chemical processes may be repeatedly performed, and the synthesized compound may have calculated functional groups on the surface thereof. Various chemical synthesis methods may be used to synthesize a dendrimer, and particularly applicable chemical synthesis methods may be more widely used.

Dendrimers may be synthesized by selecting the compounds for forming branch terminals, compounds to serve as a monomer for forming dendritic structures, and compounds for forming a core. For example, triphenylamine may be used as the compound for forming the core, and one or more compounds selected from the group consisting of acetylene, vinylene phenylene, fluorene, phenylene ethynylene, naphthalene, anthracene, tetracene, perylene, and pyrene may be used as the monomer for forming dendritic structures. The dendrimer having a triphenylamine core according to example embodiments may be synthesized using a convergence method, a divergence method, or a combination thereof.

The dendrimer may be synthesized into a larger molecule using a convergence method or a divergence method. For example, when Stb-vinyl dendron is bonded with 4-(bis(4-bromophenyl)amino)benzaldehyde through a Heck coupling reaction, which may form a carbon-carbon double bond (C=C), the dendrimer may be grown by one generation. Furthermore, when the formed aldehyde is converted into a carbon-carbon double bond (C=C) through a Wittig reaction and reacts with 3,5-dibromo benzaldehyde through a Heck coupling reaction, a larger dendrimer may be synthesized.

An organic memory device according to example embodiments may include an organic active layer sandwiched between a first electrode and a second electrode, wherein the organic active layer may include the dendrimer having a triphenylamine core according to example embodiments. FIG. 1 is a schematic sectional view showing an organic memory device according to example embodiments. Referring to FIG. 1, the organic memory device 100 may include an organic active layer 20 sandwiched between a first electrode 10 and a second electrode 30. When voltage is applied to the memory device 100, the resistance of the organic active layer 20 may exhibit bistability, thereby realizing memory characteristics. Furthermore, because the memory characteristics may be exhibited as a result of the characteristics of organic materials and may be maintained even in the absence of electrodes, the organic memory device according to example embodiments may possess nonvolatility.

The organic active layer 20 of the organic memory device 100 may exhibit conductivity and bistability. The dendrimer having a triphenylamine core according to example embodiments may have electron or hole conductivity because of conjugation (e.g., conjugated molecules). In the dendrimer having a triphenylamine core according to example embodiments, bistability may be realized as a result of the charge transfer between the triphenylamine core and the conjugated dendron in the dendrimer.

When voltage is applied to the organic memory device 100, the triphenylamine, located at the core of the dendrimer in the organic active layer 20, may emit electrons, and the emitted electrons may be transferred to the conjugated dendron. The organic active layer 20, which may be formed of the dendrimer having a triphenylamine core, may maintain substantially the same state until a different voltage is applied thereto, and the state may be maintained even after a power source is turned off. Accordingly, the organic memory device 100 according to example embodiments may exhibit improved nonvolatility. In addition to having increased coatability, the dendrimer may more accurately maintain the chemical structures of materials and may exhibit memory characteristics by trapping charges.

In addition to the dendrimer according to example embodiments, conductive polymers, (e.g., polythiophene, polyvinylcarbazole, polyaniline, polypyrrole, polyphenylenevinylene, polyfluorene, polyacetylene) may be used as the material for the organic active layer 20. For example, the conductive polymers may include poly(9-vinylcarbazole), polyaniline (emeraldine base), poly[2-methoxy-5-(2-ethylhexyloxy)-1,4-phenylenevinylene], and poly(9,9-didodecylfluorenyl-2,7-eneethinylene).

Furthermore, the organic active layer 20 may include additional electron-donating compounds, other than the dendrimer having a triphenylamine core. The electron-donating compound may be one or more compounds selected from the group consisting of tetracene, pentacene, rubrene, perylene, pyranylidene, chalcogenoaren, tetrachalcogenafulvalene, tetrathiafulvalene, tetrathionaphthalene, tetraselenaperylene, and derivatives thereof.

Figure 2:
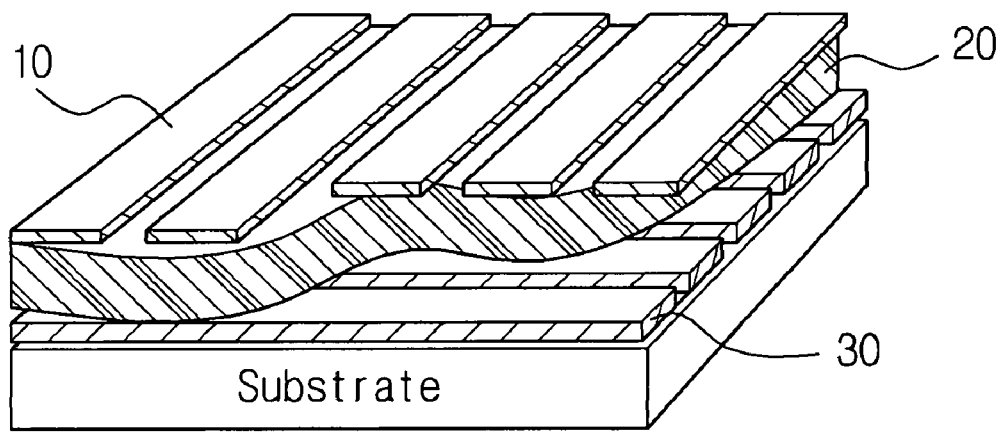
FIG. 2 is a schematic perspective view showing a memory matrix fabricated using the organic memory device according to example embodiments.

FIG. 2 is a schematic perspective view showing a memory matrix fabricated using the organic memory device according to example embodiments. As shown in FIG. 2, the memory matrix may be formed on a suitable substrate. In the memory matrix, a plurality of memory cells, formed at the intersections of the first electrodes 10 and the second electrodes 30, may exhibit bistability. The first electrode 10 and the second electrode 30 may be formed using conventional methods, e.g. thermal deposition, sputtering, e-beam evaporation, spin coating.

Suitable substrates may include organic or inorganic substrates, e.g., flexible substrates. Furthermore, a suitable substrate may include, but is not limited to, a glass substrate, a silicon substrate, a surface-reformed glass substrate, a polypropylene substrate, an activated acrylamide ceramic substrate, a membrane substrate, a gel substrate, and an aerogel substrate.

The first electrode 10 and the second electrode 30 may be formed of one or more conductive materials selected from the group consisting of metals, metal alloys, metal nitrides, metal oxides, metal sulfides, conductive polymers, organic conductors, nanostructures, and crystals. For example, the material for forming an electrode may include, but is not limited to, gold (Au), silver (Ag), platinum (Pt), copper (Cu), cobalt (Co), nickel (Ni), tin (Sn), titanium (Ti), tungsten (W), aluminum (Al), and indium tin oxide (ITO).

Examples of conductive polymers may include phenylpolyacetylene polymers, e.g., polydiphenylacetylene, poly(t-butyl)diphenylacetylene, poly(trifluoromethyl) diphenylacetylene, poly(bistrifluoromethyl)acetylene, polybis(t-butyldiphenyl)acetylene, poly(trimethylsilyl)diphenylacetylene, poly(carbazole)diphenylacetylene, polydiacetylene, polyphenylacetylene, polypyridineacetylene, polymethoxyphenylacetylene, polymethylphenylacetylene, poly(t-butyl) phenylacetylene, polynitrophenylacetylene, poly(trifluoromethyl)phenylacetylene, poly(trimethylsilyl)phenylacetylene, and derivatives thereof. Furthermore, other conductive polymers may include polyaniline, polythiophene, polypyrrole, polysilane, polystyrene, polyfuran, polyindole, polyazulene, polyphenylene, polypyridine, polybipyridine, polyphthalocyanine, poly(ethylenedioxythiophene), and derivatives thereof.

Figure 3:
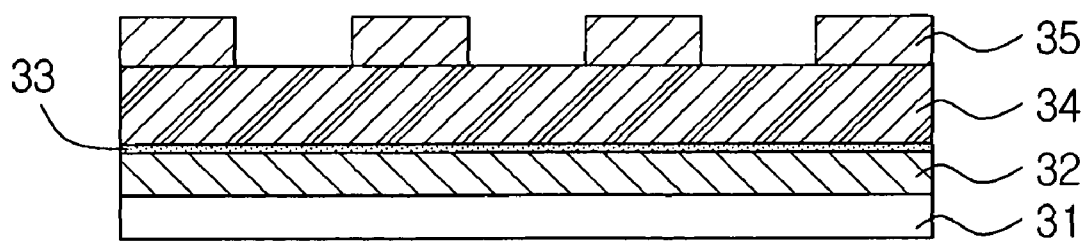
FIG. 3 is a schematic sectional view showing an organic memory device according to example embodiments.

FIG. 3 is a schematic sectional view showing an organic memory device further including a barrier layer according to example embodiments. Referring to FIG. 3, the organic memory device according to example embodiments may include a barrier layer 33 formed beneath the first electrode 35 and/or on the second electrode 32 so as to protect the first electrode 35 and/or the second electrode 32.

Figure 4:
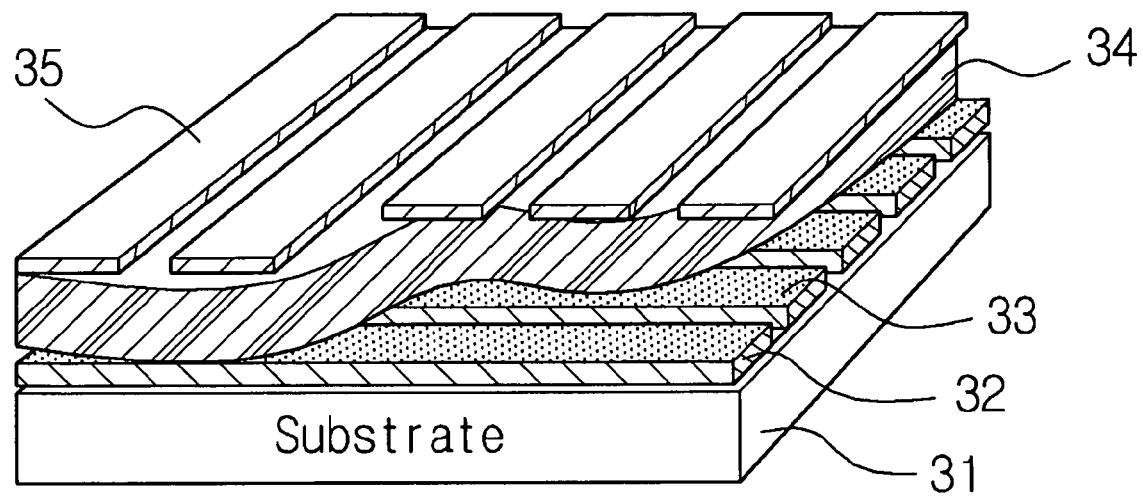
FIG. 4 is a schematic perspective view showing a memory matrix fabricated using the organic memory device according to example embodiments.

FIG. 4 is a schematic perspective view showing a memory matrix fabricated using the organic memory device having a barrier layer according to example embodiments. As shown in FIGS. 3 and 4, second electrodes 32 may be formed on a substrate 31. A barrier layer 33 may be formed on the second electrodes 32. An organic active layer 34 and first electrodes 35 may be sequentially formed on the barrier layer 33.

The barrier layer 33 may include a material selected from the group consisting of LiF, $SiO_x$, $AlO_x$, $NbO_x$, $TiO_x$, $CrO_x$, $VO_x$, $TaO_x$, $CuO_x$, $MgO_x$, $WO_x$, and $AlNO_x$. For example, the barrier layer 33 may include material selected from the group consisting of $SiO_2$, $Al_2O_3$, $Cu_2O$, $TiO_2$, and $V_2O_3$. Furthermore, the barrier layer 33 may be formed of an organic material (e.g., $Alq_3$, polymethylmethacrylate, polystyrene, polyethylene terephthalate (PET)). The thickness of the barrier layer 33 may be in the range of about 20 Å to about 300 Å.

The organic memory device according to example embodiments may be used for computers, portable information apparatuses, mobile phones, medical instruments, radar equipment, satellite equipment, and other appropriate devices and may be manufactured to have a smaller size and a lighter weight. Accordingly, when the organic memory device according to example embodiments is used for mobile phones, PDAs, notebook computers, digital cameras, portable multimedia players, DMB terminals, and other appropriate devices, portability may be improved.

A method of manufacturing an organic memory device according to example embodiments may involve using a dendrimer having a triphenylamine core. When a memory device including an organic active layer between a first electrode and a second electrode is manufactured using the method according to example embodiments, the organic active layer may be formed using a dendrimer having a triphenylamine core. The materials for the substrate, electrode, and organic active layer may be the same as that described with reference to the organic memory device above.

The method of forming an organic active layer using a dendrimer having a triphenylamine core may include, but is not limited to, spin coating, spray coating, electrostatic coating, dip coating, blade coating, roll coating, and ink jet printing. The thickness of the organic active layer may be in the range of about 50 Å to about 3000 Å.

The types of solvents that may be used in the spin coating process are not limited as long as the solvents are capable of dissolving a dendrimer having a triphenylamine core. For example, the solvent may be selected from the group consisting of chloroform, N-methylpyrrolidone, acetone, cyclopentanone, cyclohexanone, methylethylketone, ethyl cellosolve acetate, butylacetate, ethyleneglycol, toluene, xylene, tetrahydrofuran, dimethylformamide, chlorobenzene, and acetonitrile. The solvents may be used individually or in combination (e.g., mixing two or more solvents in a predetermined ratio).

The coating of the organic active layer may be baked, wherein the baking method may differ depending on the kind of solvent used. For example, the organic active layer may be baked on a relatively hot plate for about 10 minutes or more in consideration of the boiling point of the solvent. The first electrode and second electrode may be formed using conventional methods, e.g., thermal deposition, sputtering, e-beam evaporation, spin coating.

Hereinafter, example embodiments will be described in detail with reference to the examples below. The examples have been provided for purposes of illustration only and are not to be construed to limit example embodiments.

PREPARATION EXAMPLE 1
Synthesis of 3STB-TAD
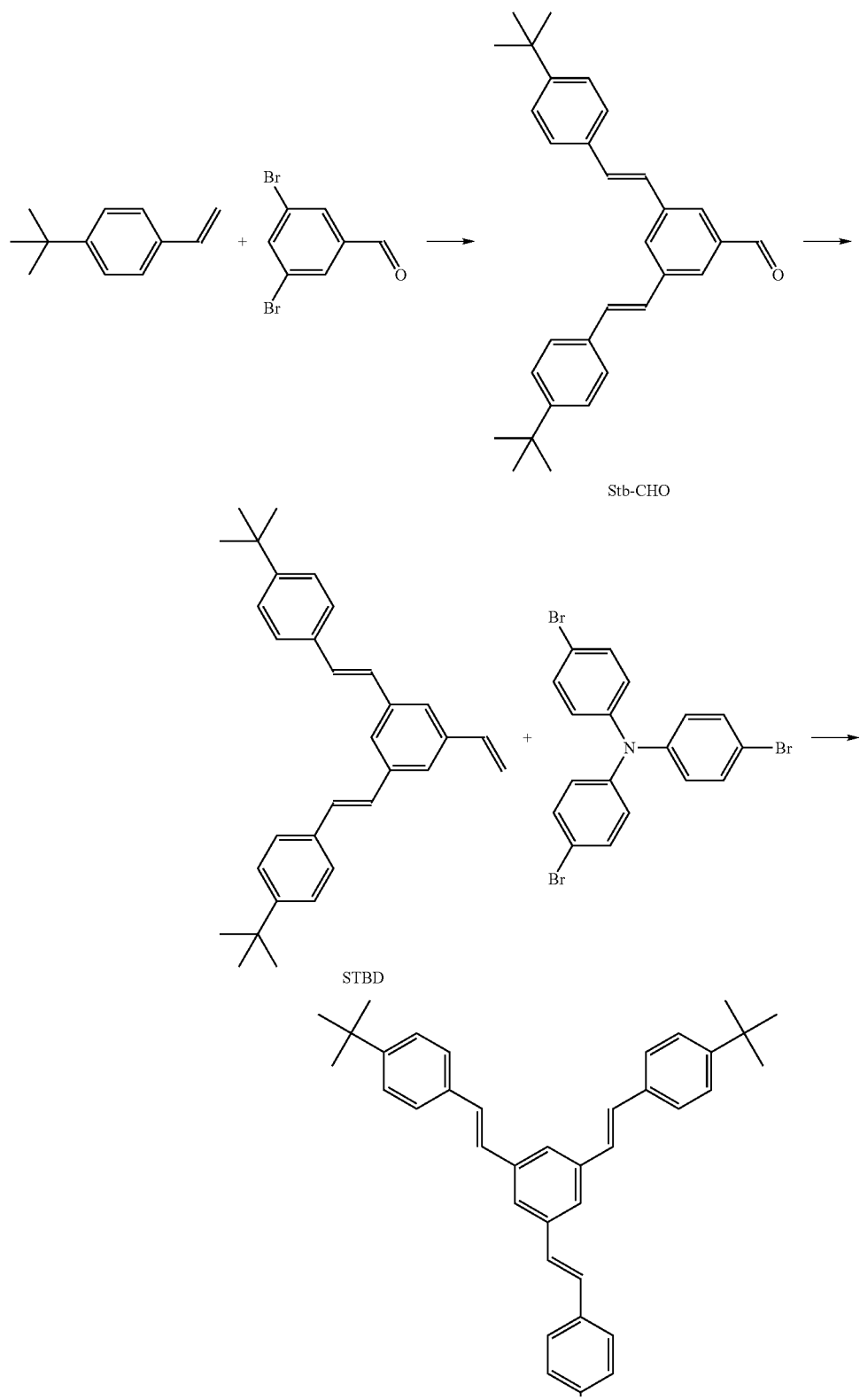

-continued

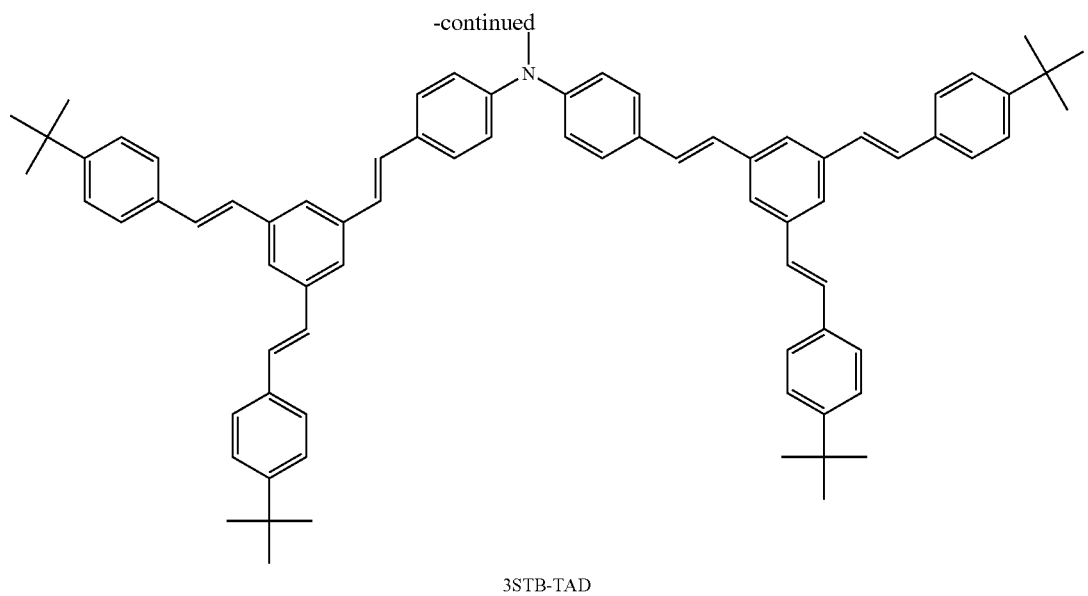

3STB-TAD

As shown in Equation 1, 3,5-dibromo benzaldehyde and 4-tert-butyl styrene were stirred in dimethylacetamide (DMAC) together with sodium carbonate, 2,6-di-tert-butyl-cresol, and a palladium catalyst at a temperature of 130° C. for 48 hours. After the reaction was completed, the reaction mixture was diluted with methylene chloride (MC) and was then washed in water to separate an organic material layer. Then, the separated organic material layer was extracted therefrom, and was adsorbed on silica gel. Subsequently, dendron Stb-CHO was separated from the organic material layer, adsorbed on silica gel, through column chromatography, in which a subsidiary solvent having a volume ratio of hexane and methylene chloride of 2:1 (v/v) was used as a developing solvent.

To grow the synthesized dendron Stb-CHO by a generation, the Stb-CHO was put into a tetrahydrofuran (THF) solution together with methyltriphenylphosphonium iodide and potassium tert-butoxide and was stirred at room temperature for 3 hours. The reaction mixture was formed into Stb-vinyl dendron through column chromatography.

Figure 5:
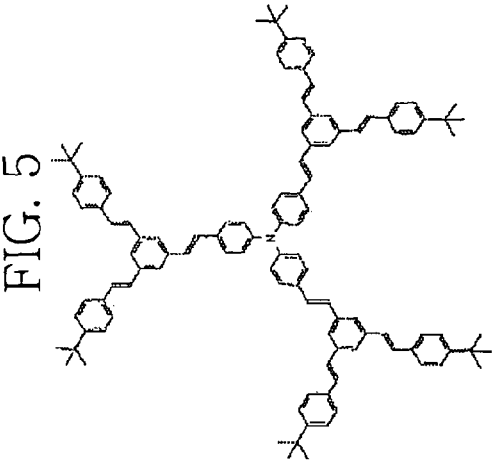
FIGS. 5 and 6 are graphs showing the analysis results of a dendrimer having a triphenylamine core according to example embodiments, obtained in Preparation Example 1, using $^1$H-NMR and $^{13}$C-NMR, respectively.
Figure 5:
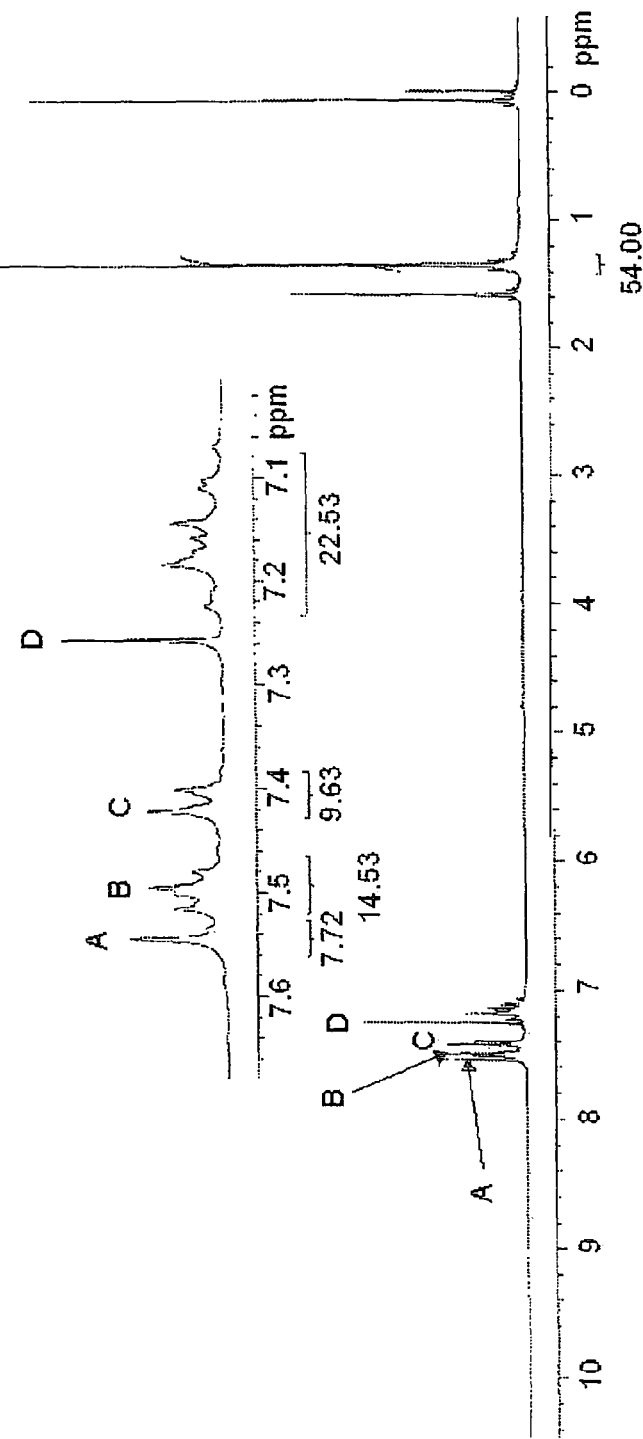
Figure 6:
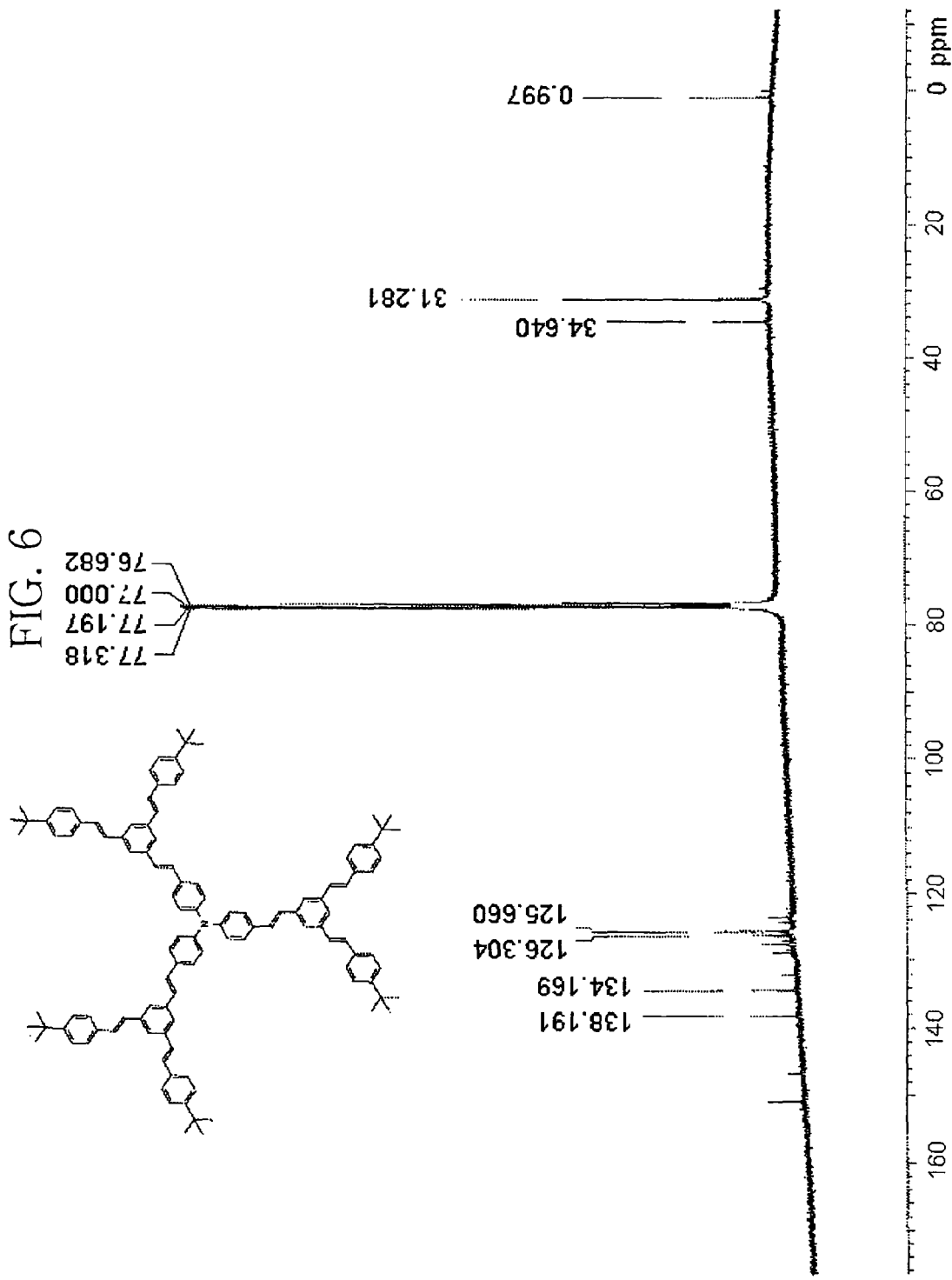
Figure 7:
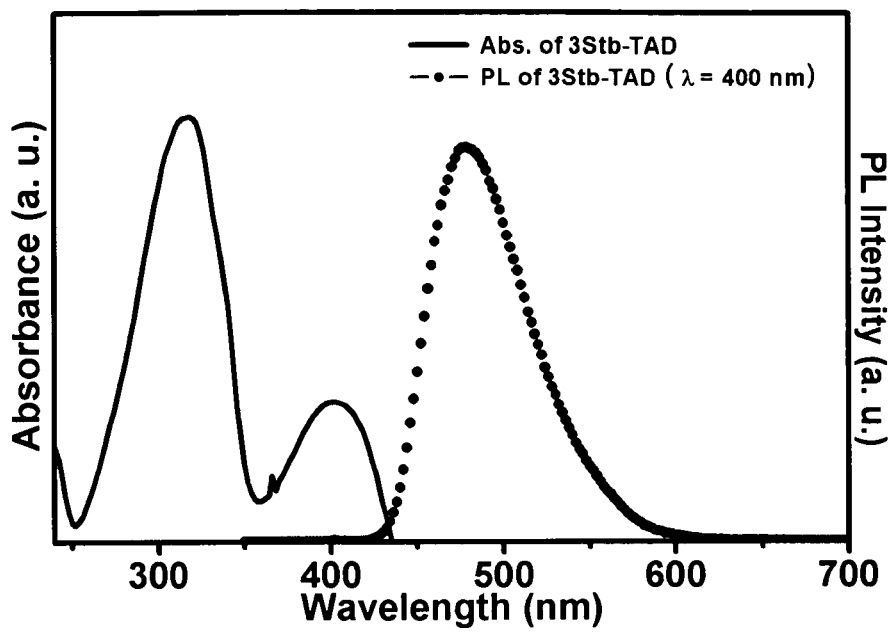
FIG. 7 is a graph showing the absorbance and photoluminescence (PL) intensity of a dendrimer having a triphenylamine core according to example embodiments and obtained in Preparation Example 1.

The previously synthesized Stilbene type dendron (STBD) was stirred in dimethylacetamide (DMAC) together with tris (4-bromophenyl)amine, sodium carbonate, 2,6-di-tert-butyl-cresol and a palladium catalyst at a temperature of 130° C. for 48 hours. It was found that a compound (triphenylamine-cored, stilbene-type dendrimer (3STB-TAD)), in which tris (4-bromophenyl)amine is entirely substituted with three bromides, and a compound in which tris(4-bromophenyl)amine is substituted with only two bromides were included in the reaction mixture through TLC (Thin Layer Chromatography) and MALDI-TOF (Matrix assisted laser desorption/ionization time-of-flight mass spectrometry). After the reaction was completed, the reaction mixture was diluted with methylene chloride (MC) and was then washed in water to separate an organic material layer. The separated organic material layer was extracted therefrom, and was adsorbed on silica gel. Subsequently, 3STB-TAD, represented by Formula 2, was separated from the organic material layer adsorbed on silica gel through column chromatography, in which a subsidiary solvent having a volume ratio of hexane and methylene chloride of 5:1 (v/v) was used as a developing solvent. Simultaneously the compound in which tris(4-bromophenyl)amine was substituted with only two bromides was also separated therefrom through column chromatography. This separated 3STB-TAD dendrimer was found and analyzed using $^1$H-NMR and $^{13}$C-NMR, and the results thereof are shown in FIGS. 5 and 6, respectively. FIG. 7 shows the absorbance and photoluminescence (PL) intensity of the separated 3STB-TAD dendrimer based on wavelength.

Example 1

A glass substrate (Corning 1737) deposited with ITO was cut to a size of 0.5 mm×0.5 mm and patterned using photolithography and wet etching methods. The substrate was dipped into acetone and isopropyl alcohol, ultrasonically treated for 15 minutes, and dried. To form an organic active layer, 10 mg of the 3STB-TAD dendrimer obtained in Preparation Example 1 was put into 1 ml of chlorobenzene ($C_6H_5Cl$), and ultrasonically treated for 30 minutes, thus being dissolved to obtain a mixed solution. The mixed solution was passed through a syringe filter made of PTFE having 0.2 μm pores, and the glass substrate deposited with ITO was then spin-coated thereon with the mixed solution at a speed of 2000 rpm for 30 seconds. The coated substrate was baked on a hot plate at a temperature of 110° C. for 10 minutes, and thus the remaining solvent was removed therefrom. In this case, the thickness of the organic active layer was about 50~100 nm, which was measured using an alpha-step profilometer. This substrate was provided with a shadow mask and put into a thermal evaporator, and then LiF was deposited to a thickness of 5 nm on the substrate to form a barrier layer. Aluminum (Al), serving as the upper electrode, was deposited to a thickness of 80 nm on the barrier layer through a thermal evaporation method, thereby manufacturing the organic memory device of example embodiments.

EXPERIMENTAL EXAMPLE

Switching Characteristics Test of Memory Device

The electrical characteristics of the memory device obtained in Example 1 were evaluated using a Keithley 4200 semiconductor characteristics analysis system. The switching characteristics of the memory device manufactured in Example 1 were evaluated depending variation in current and resistance by applying voltage to the memory device, and the results thereof are shown in FIG. 8.

Figure 8:
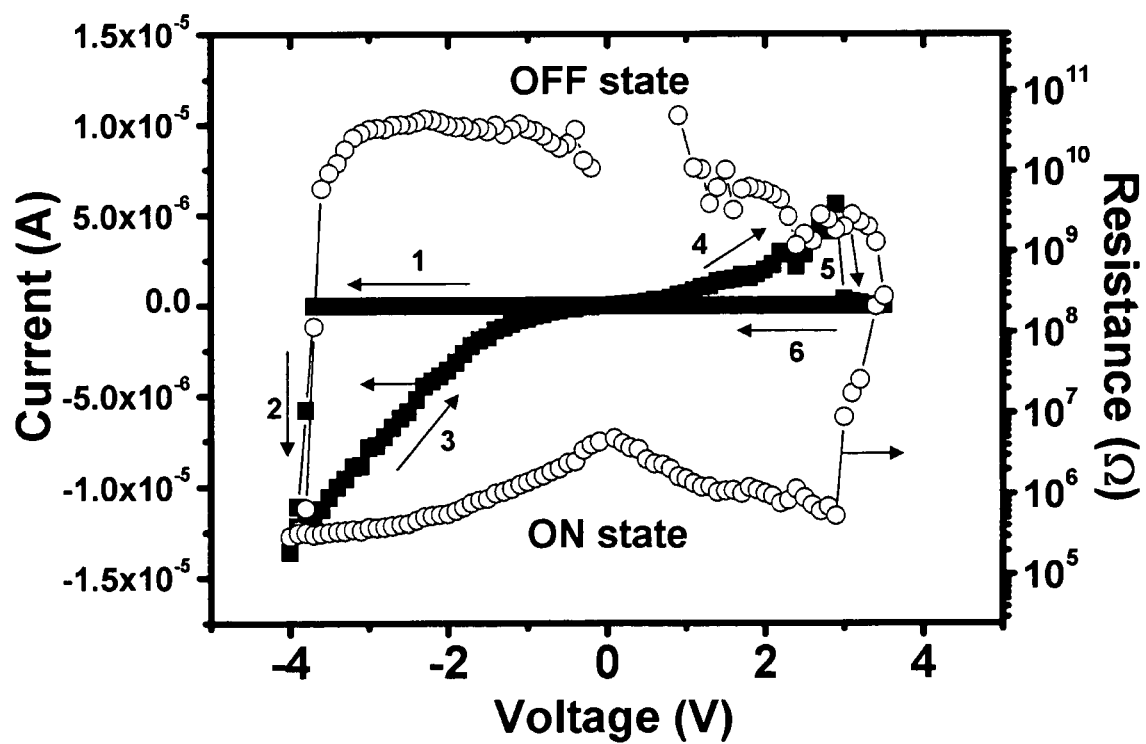
FIG. 8 is a graph showing the variation of current and resistance based on the voltage applied to the organic memory device manufactured in Example 1 according to example embodiments.

Referring to FIG. 8, two conducting states are shown in the case where the memory device was swept in two +/− directions, based on a maximum voltage of 4V. When the memory device was swept by applying a negative bias voltage thereto, the characteristics of the memory device were changed into a low resistance state (SET state) at about −4 V, and a resistance state of 0 V was also maintained. In contrast, when the memory device was swept by applying a positive voltage thereto, the characteristics of the memory device were switched into a high resistance state (RESET state) at about 3 V. Accordingly, it was found that these two different resistance states were reversibly switched. It was found that these two different resistance states could be maintained for a relatively long period of time even when voltage or current was not applied thereto. FIG. 9 shows the variation in resistance based on time in the organic memory device manufactured in Example 1 according to example embodiments. Referring to FIG. 9, it may be observed that two different resistance states were maintained for about 5000 seconds. From these results, it may be concluded that the memory device according to example embodiments exhibits bistability (e.g., two resistances at substantially the same applied voltage) and, thus, may be used as a nonvolatile memory.

The organic memory device according to example embodiments may be manufactured to have a smaller size, shorter switching time, lower operation voltage, lower manufacturing cost, and higher reliability, compared to an inorganic memory device, thereby realizing a relatively lightweight and more integrated higher-capacity memory device. Furthermore, because the organic memory device according to example embodiments may be manufactured using a lower-cost and simpler process (e.g., spin coating process) and may be processed at lower temperatures, the organic memory device may be applied to a flexible memory device.

While example embodiments have been disclosed herein, it should be understood that other variations may be possible. Such variations are not to be regarded as a departure from the spirit and scope of example embodiments of the present disclosure, and all such modifications as would be obvious to one skilled in the art are intended to be included within the scope of the following claims.

What is claimed is:

1. An organic memory device, comprising
an organic active layer between a first electrode and a second electrode; and
a barrier layer between the first electrode and the second electrode,
wherein the organic active layer includes a dendrimer including a triphenylamine core, wherein a conjugated dendron having no heteroatoms is coupled to the triphenylamine core, wherein the dendrimer is represented by Formula 1,

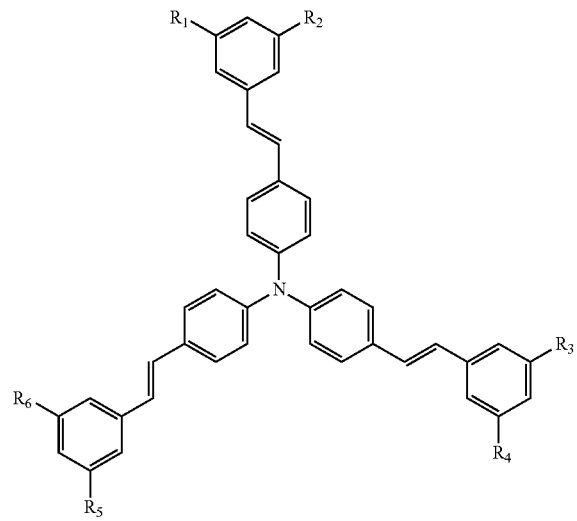

Formula 1 wherein
$R_1$, $R_2$, $R_3$, $R_4$, $R_5$, and $R_6$ are selected from the group consisting of acetylene, vinylene phenylene, fluorene, phenylene ethynylene, naphthalene, anthracene, tetracene, perylene, and pyrene, and
substituents of the $R_1$, $R_2$, $R_3$, $R_4$, $R_5$, and $R_6$ are selected from the group consisting of $C_1$-$C_{20}$ alkyl, $C_3$-$C_{20}$ cycloalkyl, $C_5$-$C_{30}$ heterocycloalkyl, $C_2$-$C_{20}$ alkenyl, $C_6$-$C_{20}$ aryl, $C_5$-$C_{30}$ heteroaryl, $C_7$-$C_{20}$ arylalkyl, and $C_7$-$C_{30}$ heteroarylalkyl,
wherein the barrier layer includes a material selected from the group consisting of $SiO_2$, $Al_2O_3$, $Cu_2O$, $TiO_2$, $V_2O_3$, $Alq_3$, polymethylmethacrylate, polystyrene, and polyethylene terephthalate (PET).

2. The organic memory device according to claim 1, wherein the dendrimer represented by Formula 1 is further represented by Formulas 2 to 4,

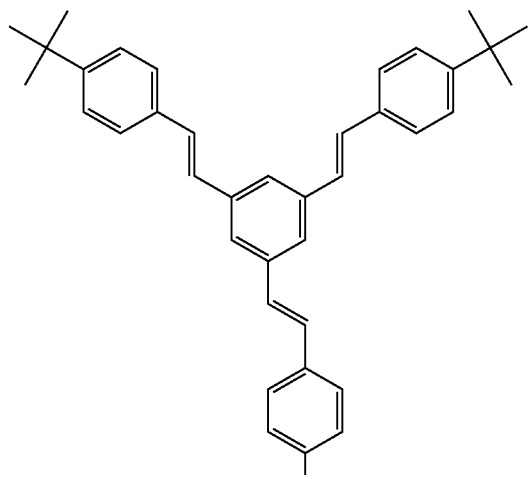

Formula 2

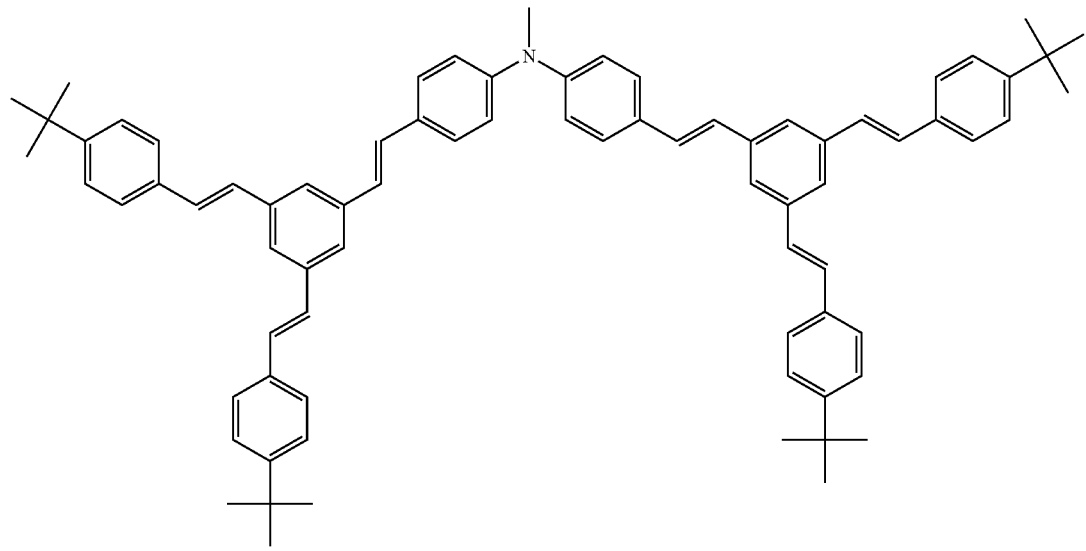
Formula 3
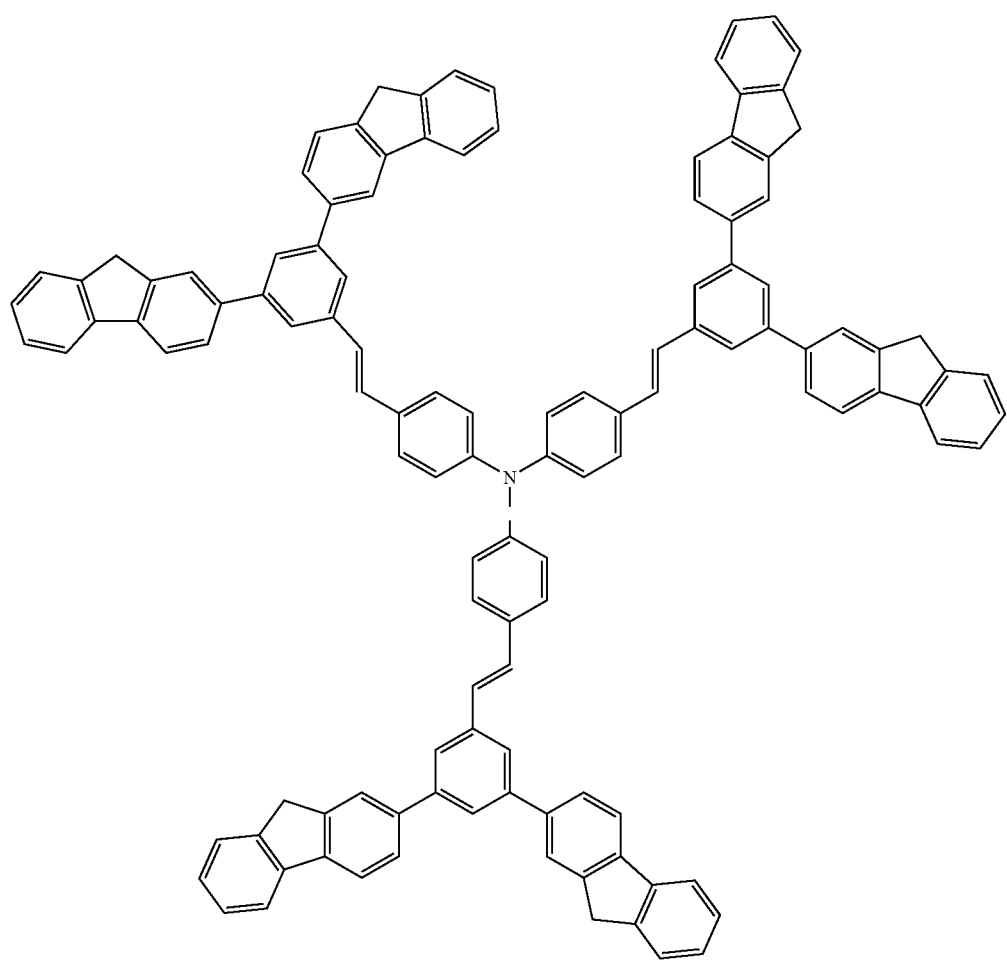

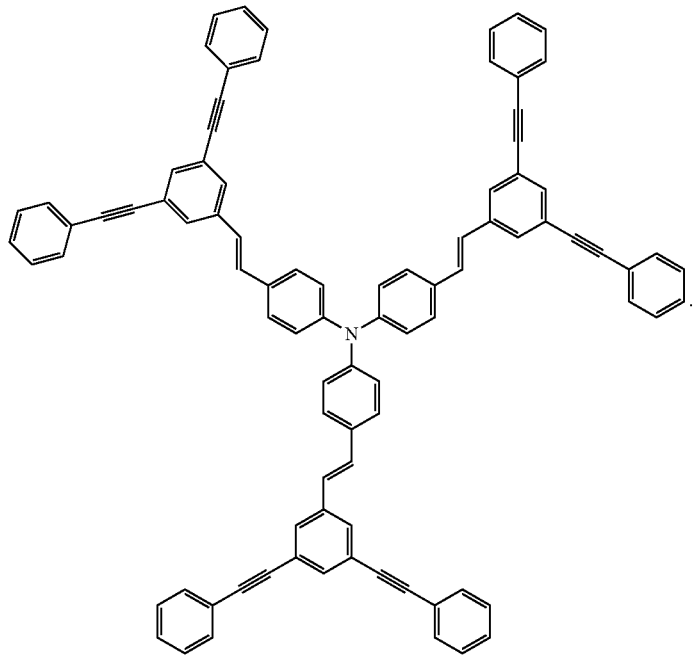

3. The organic memory device of claim 1, wherein at least one of the first electrode and the second electrode is formed of at least one material selected from the group consisting of metals, metal nitrides, metal oxides, metal sulfides, conductive polymers, organic conductors, and crystals.

4. The organic memory device of claim 3, wherein the conductive polymer is selected from the group consisting of polydiphenylacetylene, poly(t-butyl)diphenylacetylene, poly(trifluoromethyl)diphenylacetylene, poly(bistrifluoromethyl)acetylene, polybis(t-butyldiphenyl)acetylene, poly(trimethylsilyl)diphenylacetylene, poly(carbazole)diphenylacetylene, polydiacetylene, polyphenylacetylene, polypyridineacetylene, polymethoxyphenylacetylene, polymethylphenylacetylene, poly(t-butyl)phenylacetylene, polynitrophenylacetylene, poly(trifluoromethyl)phenylacetylene, poly(trimethylsilyl)phenylacetylene, polyaniline, polythiophene, polypyrrole, polysilane, polystyrene, polyfuran, polyindole, polyazulene, polyphenylene, polypyridine, polybipyridine, polyphthalocyanine, poly(ethylenedioxythiophene), and derivatives thereof.

5. The organic memory device of claim 1, wherein at least one of the first electrode and the second electrode is formed of at least one material selected from the group consisting of gold (Au), silver (Ag), platinum (Pt), copper (Cu), cobalt (Co), nickel (Ni), tin (Sn), titanium (Ti), tungsten (W), aluminum (Al), and indium tin oxide.

6. A method of manufacturing the organic memory device of claim 1, comprising:
    forming the organic active layer between the first electrode and the second electrode; and
    forming the barrier layer between the first electrode and the second electrode.

7. The method of claim 6, wherein the dendrimer represented by Formula 1 is further represented by Formulas 2 to 4, Formula 2

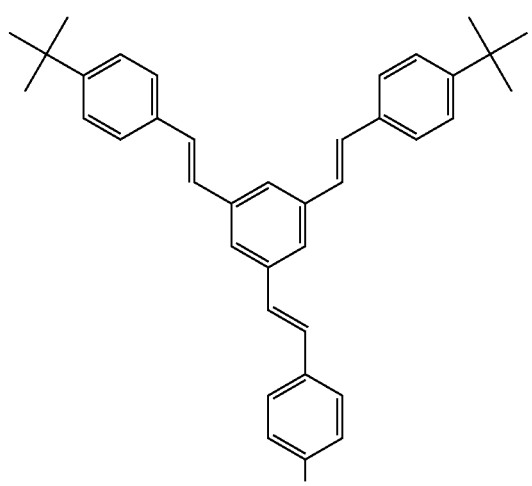

-continued
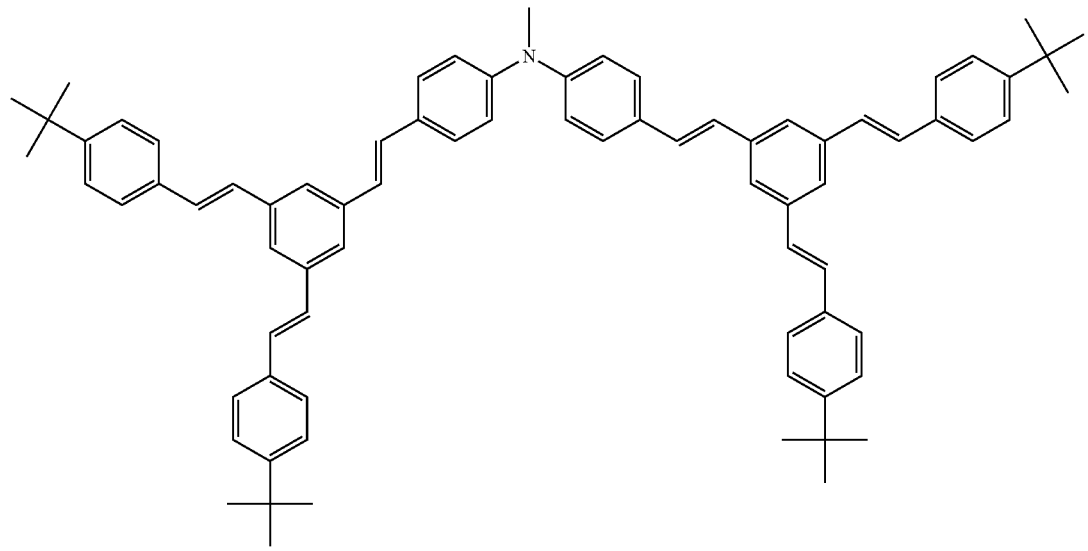
Formula 3
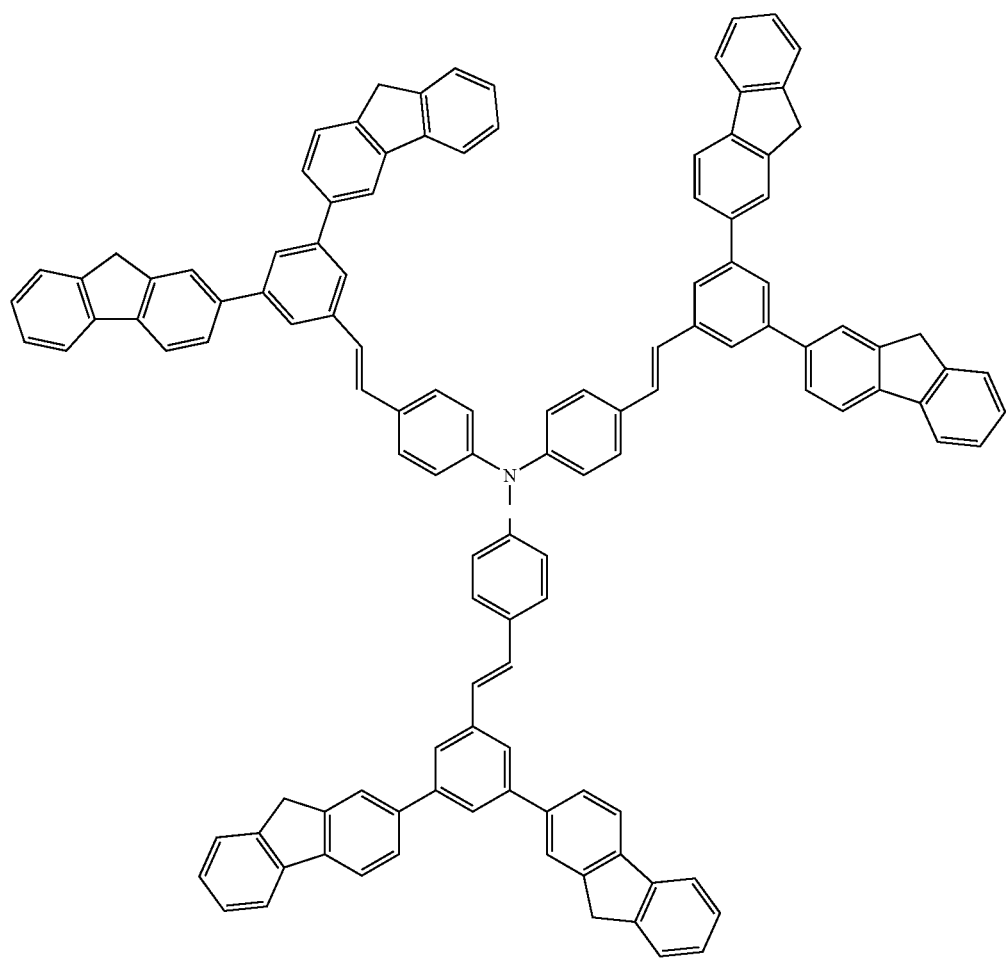

Formula 4

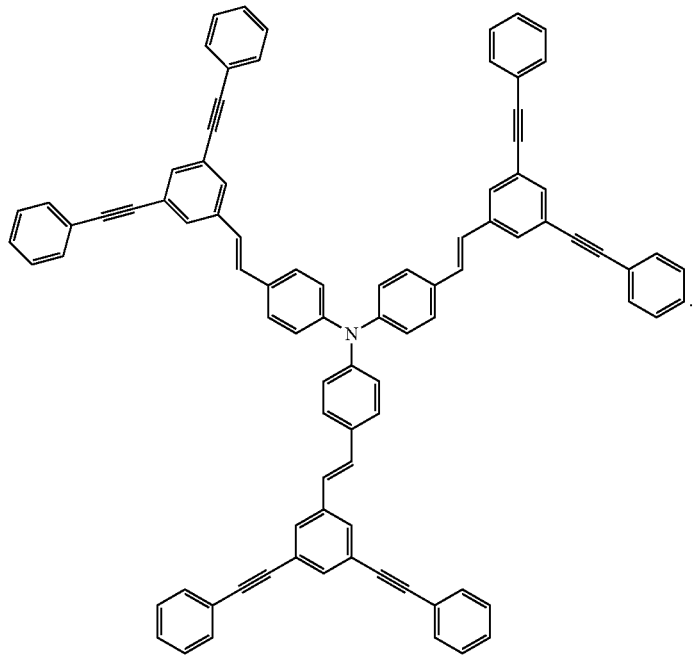

8. The method of claim 6, wherein the organic active layer is formed by applying the dendrimer using a method selected from the group consisting of spin coating, spray coating, electrostatic coating, dip coating, blade coating, roll coating, and ink jet printing.

9. The method of claim 6, wherein forming the organic active layer includes providing a solvent with the dendrimer, the solvent being at least one material selected from the group consisting of chloroform, N-methylpyrrolidone, acetone, cyclopentanone, cyclohexanone, methylethylketone, ethyl cellosolve acetate, butylacetate, ethyleneglycol, toluene, xylene, tetrahydrofuran, dimethylformamide, chlorobenzene, and acetonitrile.

10. The method of claim 6, wherein at least one of the first electrode and the second electrode is formed of at least one material selected from the group consisting of metals, metal nitrides, metal oxides, metal sulfides, conductive polymers, organic conductors, and crystals.

* * * * *